United States Patent [19]

Reents

[11] Patent Number: 4,895,160
[45] Date of Patent: Jan. 23, 1990

[54] APPARATUS FOR MEASURING THE LIFE FUNCTIONS OF A HUMAN BEING, PARTICULARLY AN INFANT

[76] Inventor: Heinrich Reents, Magnolienweg 23, 475 Unna, Fed. Rep. of Germany

[21] Appl. No.: 886,112

[22] Filed: May 22, 1986

[51] Int. Cl.$^4$ .............................................. A61B 5/02
[52] U.S. Cl. .................................... 128/671; 128/722
[58] Field of Search ............... 128/670, 671, 721, 722, 128/725, 782; 340/573, 666

[56] References Cited

U.S. PATENT DOCUMENTS

| | | | |
|---|---|---|---|
| 3,898,981 | 8/1975 | Basham | 128/722 |
| 3,926,177 | 12/1975 | Hardway, Jr. et al. | 128/2 |
| 3,991,746 | 11/1976 | Hanna | 128/722 |
| 4,359,726 | 11/1982 | Lewiner et al. | 340/666 |
| 4,381,788 | 5/1983 | Douglas | 128/722 |
| 4,438,771 | 3/1984 | Friesen et al. | 128/671 |
| 4,474,185 | 10/1984 | Diamond | 128/722 |
| 4,551,713 | 11/1985 | Aossey | 340/666 |

FOREIGN PATENT DOCUMENTS 2534132  4/1984  France .................................. 128/670

Primary Examiner—Max Hindenburg
Assistant Examiner—John P. Lacyk
Attorney, Agent, or Firm—Hill, Van Santen, Steadman & Simpson

[57] ABSTRACT

A method and apparatus are provided for measuring life functions of a human being, particularly an infant, by way of a support acting on the basis of pressure changes as a life condition monitor which also comprises temperature sensors, humidity sensors, and the like and acts on the measuring and display device connected to the support and functioning in response to pressure changes. The method and apparatus are particularly characterized in that the support emits a signal which reflects the rib cage or, respectively, diaphragm motion during respiration and the motion of the cardiac muscles.

11 Claims, 3 Drawing Sheets

APPARATUS FOR MEASURING THE LIFE FUNCTIONS OF A HUMAN BEING, PARTICULARLY AN INFANT

BACKGROUND OF THE INVENTION

1. Field of the Invention

The present invention relates to a method and to an apparatus for measuring the life functions of a human being, particularly of an infant, by way of a support acting as a state-of-life monitor on the basis of pressure changes, and which also comprises temperature sensors, humidity sensors, and the like, and acts on a measuring and display device connected to the support and operating on the basis of pressure changes.

2. Description of the Prior Art

The German published application 23 45 551, and the corresponding U.S. Pat. No. 3,926,177, fully incorporated herein by this reference, discloses that the respiration, particularly a potential cessation of respiration, as well as an increased muscle activity of a human being, or of a test animal, be identified by way of a capacitively-acting support. A measuring instrument in accordance therewith has the disadvantage that only a portion of the signals necessary for the subsidiary functions can be communicated therewith. Cessation of respiration, cardiac arrests and unexplained, other causes of death such as suddenly elevated temperature, the failure of body occlusion openings, and the like, cannot be acquired.

SUMMARY OF THE INVENTION

The object of the present invention is to provide a life function measuring method and apparatus which provide information concerning the normal condition or the deviation from the normal condition, particularly concerning the deviation therefrom in a foreseeable time, under all circumstances and using the most modern electronic amplification technology.

The above object is achieved in that the support, which acts on the basis of pressure changes, emits a signal which reproduces the rib cage movement or, respectively, the diaphragm movement during respiration and the movement of the cardiac muscles and also supplies a signal for the pulse beat, particularly by way of an auxiliary sensor. The three essential indications for a normal life function are thereby reproduced and provide the first, rough grid for a display as to whether or not a life form exhibits severe malfunctions of the life functions; and given the display that severe malfunctions exit, a person (or a corresponding medical device triggered by a malfunction condition) can undertake all resuscitation actions that are necessary.

According to a particular feature of the invention, the signals of the support, which acts on the basis of pressure changes, are subjected to an image pattern recognition of a unit contained in the memory, being subjected thereto on the basis of preselected tolerance curves representing a normal condition. As a result thereof, it is possible to register deviating characters which deviate from the normal life rhythm of a life form and to recognize the same. As an image pattern, a normal life form is supplied into the corresponding apparatus, i.e. into a corresponding computer, and all deviations lying outside of the range of tolerance are displayed. Two tolerance ranges are thereby preferably displayed independently of one another, a normal tolerance range of deviations still lying within the framework of what is tolerable and a range of tolerance of deviations indicating a fatal malfunction. The personal constitution of the life form being monitored can therefore be taken into consideration.

According to another feature of the invention, the signals of the pressure-sensitive support are subjected to a frequency analysis and are further subjected to an analysis as to the amplitude level. It is possible on the basis of these two criteria to differentiate the movement of the individual muscles, for example of the cardiac muscles, of the large muscles, for example the leg and arm muscles, of the muscles of respiration and of the remaining muscles. A display of an unusual behavior occurs only when one of the corresponding tolerance limits is transgressed. It is advantageously taken into consideration that the frequencies of the cardiac muscle, for example, and of the respiration muscles, generally deviate from one another. They can be identical under special circumstances, but that is usually a symptom of a disturbed respiratory activity, particularly of an oxygen deficiency.

According to another feature of the invention, the signal evaluation occurs by way of a differential circuit. Advantageously, the differential circuit allows different weights of the life form whose life functions are to be monitored and supervised and displayed independently of its weight. A possibility of universal utilization therefore occurs without having to carry out matching and balancing to the respective life form. The requirement that monitoring be possible in a foolproof manner by simply plugging in a plug without further fihe adjustment is therefore met in the best possible manner.

According to another feature of the invention, the support acts as an active sensor independent of the weight and independent of the size of the mat, the motional energy thereof output by the human body being amplified and subjected to the image pattern analysis, to the frequency analysis or to the amplitude analysis. This is the advantageously possible construction of the life function monitoring apparatus of the invention. A further construction can provide that the mat, acting weight-independent, is divided into various fields, so that it is simultaneous possible to identify the positions of the person whose life functions are being monitored. Particularly for older persons, it is thereby possible to make a preliminary display of a condition that indicates a fall from a hospital bed.

According to another feature of the invention, the analyzed, discrete signals are separately displayed and trigger individual alarms. It is therefore possible to display the many, different dangerous conditions of a life form, particularly of a bed-ridden patient or of an infant in such a manner that the nursing personnel can react before the event occurs. It is thereby particularly advantageous that the discrete signals are subjected to a tendency analysis and that the result of the tendency analysis is displayed and fed to the individual alarm display apparatus. This broadens the possibility of the displays of positional change and of the possibility of a deterioration of the situation. Tendency analysis is already well known in the art relating to industrial systems, particularly for thermal systems, which can be applied without hesitation and also indicates the approach to precarious conditions for a person in a heretofore unobtainable manner.

The discrete signals are transmitted by teletransmission to a stationary or mobile monitoring station and are successively or simultaneously displayed and can trigger individual alarms at such a remote location. This is a possibility of supervision by a minimum of personnel which accommodates the current trend of eliminating personnel without having the occurrence of a negative influence on the patient.

According to the invention, the method is implemented by an apparatus comprising a capacitively-operating support as a life state monitor for the life function of a human, particularly of a human, which apparatus comprises a measuring and display device connected to the support for the purpose of editing and amplifying the signals transmitted from the capacitively-operating support. The apparatus contains a frequency analyzer for simple tasks, an amplitude analyzer when a more thorough reliability of the display is required, and an image pattern analyzer which comprises a comparison to a normal reaction of a life line, particularly an infant, and executes this comparison within the scope of prescribed tolerance limits, and also comprises appropriate amplification paths for the discrete signal. These are preferably identically constructed in order to correspondingly reduce the costs of the overall apparatus.

The amplification paths comprise a voltage source with an interface to the pressure-sensitive capacitative support. It is therefore guaranteed that a faulty connection cannot trigger a fatal current shock for the life form. In the past, this has repeatedly turned out to be dangerous, even though allegedly impossible. As with the design of the sensor mat, the interface therefore most essential for the evaluation of the overall invention in that it is actively operating element.

The circuit technology of the individual amplification paths shall be set forth below and may be derived in terms of all of its details from the following detailed description.

According to a particular embodiment of the invention, which exceeds the current technology of the individual amplification technology, independently of the other sensors, the pulsation of the patient, such as an infant, is transmitted in a wireless manner by a sensor applied to the skin, being transmitted to a receiver, particularly to the capacitively acting mat which records the life function. Yet another, accurate differentiation of the life function signals is therefore possible.

According to another feature of the invention, it is provided that the individual life function signals are forwarded to a central display unit which can be monitored by supervisory personnel. Therefore, a monitoring of the individual patients which was heretofore only possible in intensive care stations is established, and is far more economical and simultaneously possible without endangering the patient as a result of cables, hoses, etc. The actual construction is simple on the basis of systems of the type introduced above, for example, in air and sea travel for locating and rescuing persons. These systems operate free of disruption to an optimum degree and on the basis of economical devices produced in mass production.

BRIEF DESCRIPTION OF THE DRAWINGS

Other objects, features and advantages of the invention, its organization, construction and mode of operation will be best understood from the following detailed description, taken in conjunction with the accompanying drawings, on which.

DESCRIPTION OF THE PREFERRED EMBODIMENTS

Figure 1:
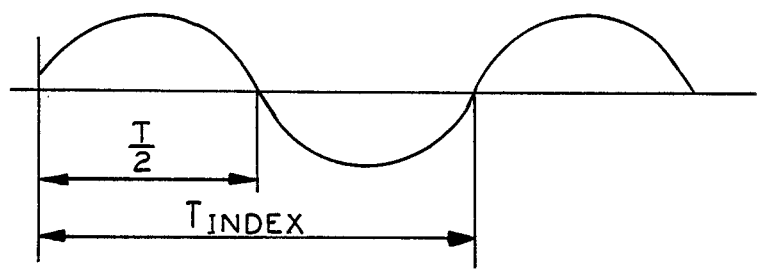
FIG. 1 is a graphic illustration of an ideal respiration signal.

FIG. 1 illustrates an idealized curve of a typical respiration signal, whereby the time duration of a breath is indicated as $T_{index}$ respiration. Half the period duration of a breath is identified as $T/2$ for what is basically an idealized sine wave.

Figure 2:
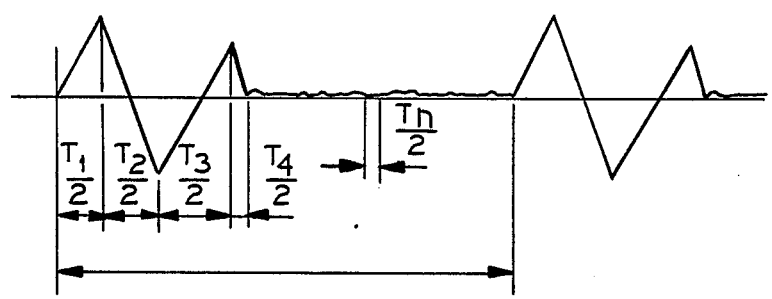
FIG. 2 is a graphic illustration of an ideal pulse signal.

The idealized curve of the pulse illustrated in FIG. 2 is more similar to a decaying, triangular wave having pauses. The repetition time of the pulse is illustrated as $T_{pulse}$. The individual, characterizing leading and trailing edges of the signal are referenced $T1/2$, $T2/2$, $T3/2$, $T4/2$ and $Tn/2$. These referenced signal portions can also be interpreted as parts of superimposed oscillations, from which it may then be seen that the pulse comprises a significantly higher proportion of higher-frequency oscillations than does the signal of respiration, although the repetition time of the respiration and that of the pulse can definitely lie on the same order of magnitude.

Figure 3:
FIG. 3 is a graphic representation of a temperature signal.

FIG. 3, by contrast, shows an assumed signal curve of temperature. It may be seen that the signal curve of the temperature need not necessarily change periodically and that the change of the signal lies on a significantly smaller order of magnitude than the amplitudes of the pulse signal or of the respiration signal.

Figure 4:
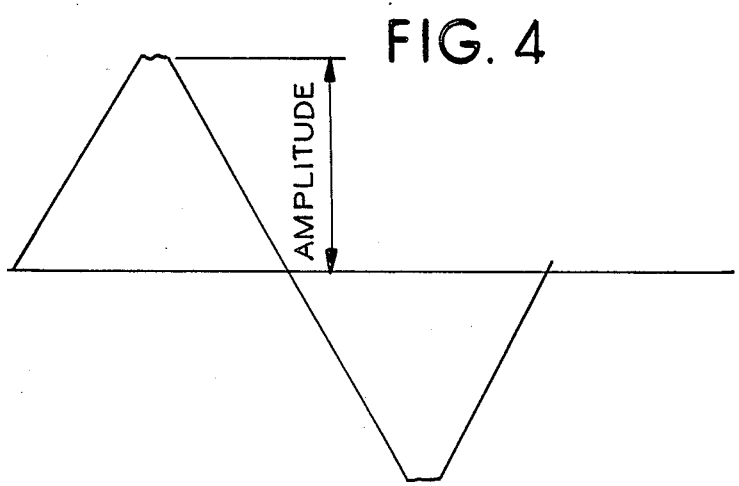
FIG. 4 is a graphic illustration of a muscle contraction signal.

By contrast, again, the signal curve in FIG. 4 relating to muscle contraction exhibits a significantly higher amplitude than the other signals. This conspicuous feature is identified by the indicated amplitude height. The curve of the signal allows conclusions to be drawn regarding the frequency content which likewise differs from the remaining signal. In accordance with the invention, the information for monitoring the various life functions is acquired from the measured signal by the analysis of the various frequencies and amplitudes.

Figure 5:
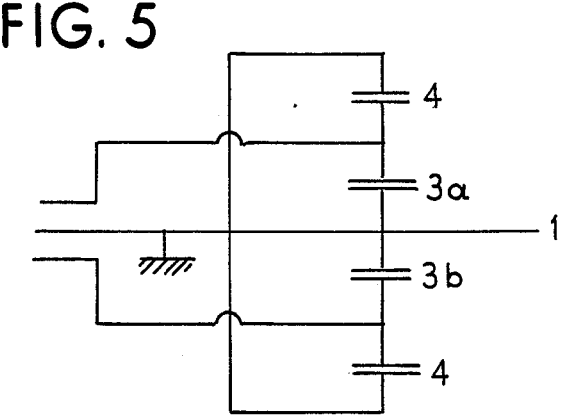
FIG. 5 is an equivalent circuit diagram of a sensor mat constructed in accordance with the present invention.

The equivalent circuit diagram of a suitable measuring sensor, operating as a signal generator, is illustrated in FIG. 5. An electric field is built up between the center aluminum foil 1 and two outer aluminum foils 3a and 3b, on the one hand, as well as between a shield 4 and two other aluminum foils 3a and 3b, on the other hand. An increase in the sensitivity is achieved by the parallel connection of four capacitors. This is schematically illustrated in FIG. 5. The shield foil is insulating at the inside and conductive at the outside. As is the case with the center foil 1, the shield foil is connected to ground potential. The shield 4 therefore fulfills the following functions:

No electrical field can penetrate from the interior to the exterior or from the exterior to the interior;

It lends the mattress a good, uniform appearance;

The grounding of the mat represents the second stage of protection for the patient against potential overvoltages;

It fulfills capacitor functions relative to the capacitor plates 3a and 3b;

It serves the purpose of reflecting the body heat, this representing an additional benefit in the case of new born infants which easily suffer from hypothermia.

The capacitor plates 3a and 3b are constructed in the form of a foil which is conductive on both sides. All foils (for example aluminum foils) are secured against dislocation by way of two-sided adhesive strips. Adhesive strips are only applied in punctiform fashion in order to not reduce the overall sensitivity of the mat. The spacing between the capacitor plates (aluminum foils) 3a and 3b is produced by an insulating spacing medium. The connection to the device of FIG. 7 is provided by way of a shielded coax cable and a diode plug.

Figure 6:
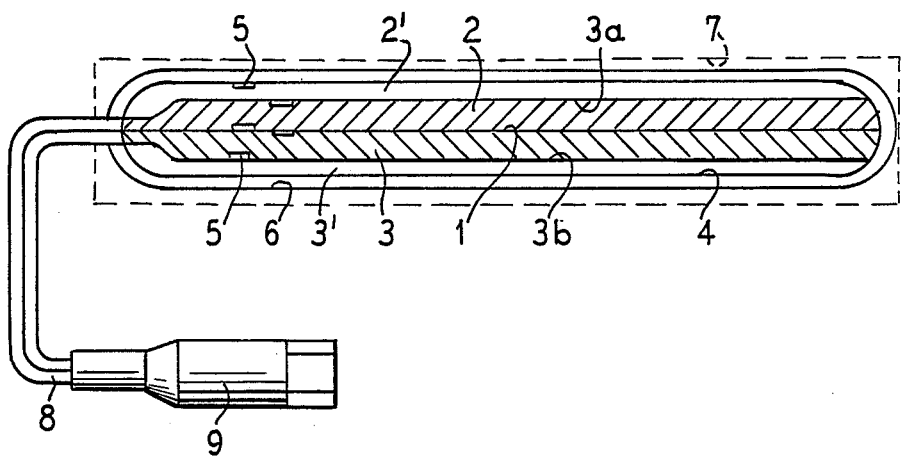
FIG. 6 is a sectional view taken through a sensor mat constructed in accordance with the present invention.

The structure of the mat is illustrated in the sectional view of FIG. 6. Again, the center aluminum foil is referenced 1, this being conductive on both sides. An insulating medium 2 is applied to one side of the foil 1 and an insulating medium 3 is applied to the other side of the foil 1. A pair of capacitor plates in the form of aluminum foils 3a and 3b are respectively applied to the insulating layers 2 and 3, the layers 3a and 3b being conductive on both sides. A further aluminum layer 4 is provided about the aforementioned elements, the layer 4 being conductive on the inside and nonconductive on the outside. Two-sided adhesive strips 5 are provided in punctiform fashion for connecting the aforementioned layers together. A polyvinylchloride (PVC) film skin 6 is provided for hygiene and insulation.

A textile covering 7 may also be provided, this not being a determining factor in operation. A shielded coax cable 8 has a diode plug 9 at the end for connecting the mat to the monitor.

Figure 7:
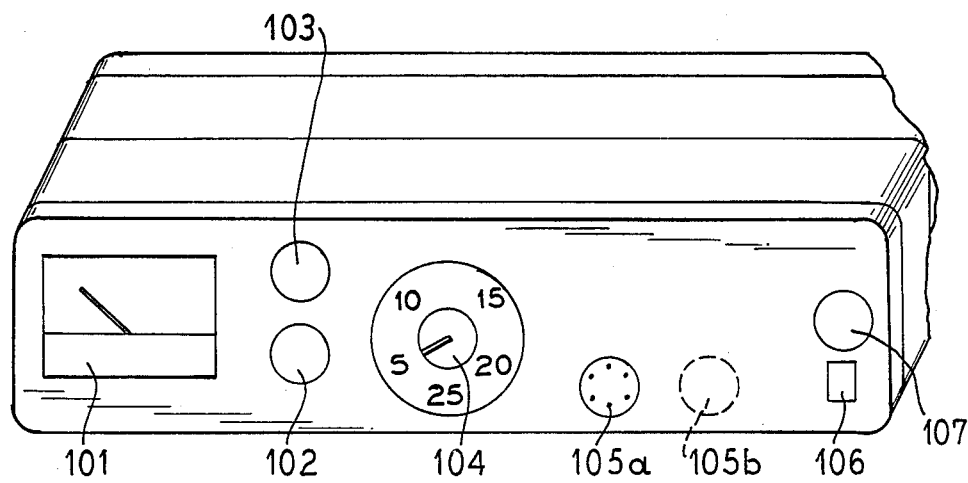
FIG. 7 is a perspective view of an electronic monitoring apparatus constructed in accordance with the present invention.

Referring to FIG. 7, the housing of the electronic monitor is illustrated. The housing may be aluminum, plastic or the like. Basically, the housing fulfills shielding functions. A display device 101 for displaying the respiration pulse is arranged in the housing. Further, a green light-emitting diode 102 is provided in the front panel of the housing and lights in synchronism with the respiration pulse. A further, red light-emitting diode 103 represents an optical alarm display. An adjustable time interval generator is referenced 104. Diode input sockets for connection of the sensor mat are referenced 105a and 105b. An on/off switch 106 is provided along with a green light-emitting diode 107 to indicate the commercial power supply. Given battery operation or, respectively, emergency operation, the light-emitting diodes 102 and 107 are automatically shut off. The supply connection and a 12 volt battery connection are provided at the rear of the housing.

Figure 8:
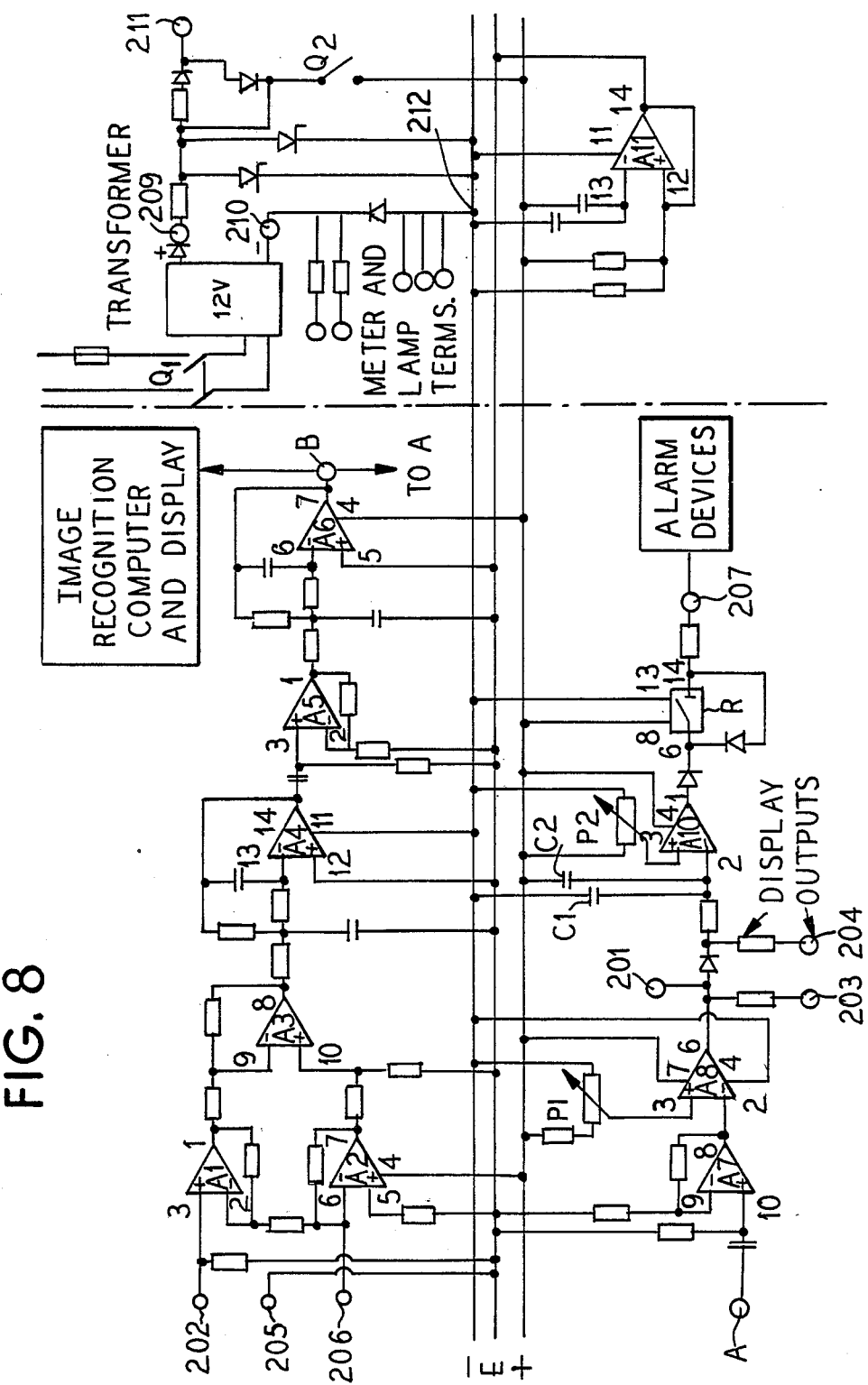
FIG. 8 is a schematic circuit diagram of an amplification system which may be employed as an amplification channel for the type of signals illustrated in FIGS. 1-4 in practicing the present invention.

The fundamental circuit of the apparatus is illustrated in FIG. 8 and will be discussed in detail below with reference to the respiration signal. This circuit essentially comprises four components, namely an amplifier unit, an evaluation and alarm unit, a power pack and emergency power supply and battery operation circuit, and a noise transmission alarm and reception unit.

The central mat foil 1 and the outer protective foil 4 are connected to the circuit via a terminal 205 which is, in turn, connected to an artificial ground E. The upper capacitor foil 3a and the lower capacitor foil 3b are respectively connected to the terminals 202 and 203. A pair of input amplifiers A1 and A2 are provided as high-resistance amplifiers for receiving the, for example, respiration signal. The output of the amplifiers A1 and A2 is fed to an amplifier A3 for amplification by a factor of 10. A further amplification at this stage is without meaning since the applied offset voltages could lead to the output of the amplifier A3 into limitation. The commercial supply hum and the high frequencies are filtered out by a low-pass filter which is an active filter including an operational amplifier A4. The upper limit frequency of the low-pass filter lies slightly below 50 Hz. A following, passive high-pass filter rids the output signal of the amplifier A4 of DC voltage components which can still pass the preceding low-pass filter. The limit frequency amounts to about 1 Hz. The signal is then amplified by a factor of 1000 in an operational amplifier A5. Due to the high input impedance of the amplifier A5, the highpass filter is not highly loaded. Noise and hum components again enter into the signal due to the amplifier A5. These are again filtered out by an active low-pass filter including an operational amplifier A6, this filter being constructed in the same manner as the active low pass filter which includes the amplifier A4. The DC components are again extracted by a following, passive, high-pass filter before the signal is again amplified by a factor of 200 with the assistance of an amplifier A7. The output signal of the stage A6 may also be fed to a computer interface for image pattern recognition stored in a memory as initially set forth.

The respiration signal has now been amplified to such a degree that it can be evaluated via a comparator having a variable reference value provided, for example, by way of a potentiometer P1. The difference between the quiescent voltage of the mattress and the reference voltage thereby amounts to 0.02 volts. Since the comparator still switches without fault given a voltage differential of 105 μv, the circuit can still be made more sensitive by a factor of 100. Too high a sensitivity, however, leads to self oscillation, for which reason the operating point should be accurately set with the assistance of an oscilloscope. Whereas integrated operational amplifiers have been employed for the circuits A1–A7, the comparator A8 requires a different module because of the required sensitivity, for example a commercially-available module designated LF 356. The output signal of the amplifer A8 is either 0 volts or 12 volts.

Each breath therefore leads to a voltage pulse at the output of the operational amplifier A8, this pulse being displayed by a green light-emitting diode (102) and forwarded to a following time function element. The time function element is composed of a capacitor C1 having, for example, a capacitance of 10 μF and connected to the negative pole, and a rotary potentiometer P2. The potentiometer P2 is preceded by a resistor having a value of, for example, 100 k ohms. The potentiometer enables a time interval setting from 0 seconds through 35 seconds.

A further capacitor C2, connected to the positive pole has the following function. Without the second capacitor, the voltage level of the first capacitor C1 always lies below the set reference voltage at the input of the operational amplifier A10 when the device has not been switched on for a period of time. This would lead to the fact that the relay triggering the alarm would trigger, since the relay is a latching relay. The second capacitor C2 increases the voltage level at the inverting input of the operational amplifier A10 above the reference voltage at the non-inverting input. The effect that the device indicates alarm immediately after being switched on is thereby suppressed. The set reference voltage should lie in the range between 0.5 volt and 1 volt. Each voltage pulse from the output of the operational amplifier A8 therefore leads to charging of the capacitor C1. This capacitor discharges via the 100 k ohm resistor and the rotary potentiometer P2 (FIG. 7, 104). When voltage pulses fail, the reference value at the non-inverting input 3 of the operational amplifier A10 is downwardly transgressed and the operational amplifier A10 connects through to drive a latching relay R. It causes illumination of the red light-emitting diode 103 in FIG. 7 which is connected to the terminal 207, which terminal is also connected to a device for generating an audible alarm signal. In more intelligent versions, the module containing the operational amplifiers A8 and A10 can optionally be replaced by a microcomputer system.

The symmetrical voltage supply which is indispensible for the operation of the operational amplifier of the module A1-A7 is generated by the operational amplifier A11. The device is fed by a stabilized power pack having an output voltage of 12 volts. The primary circuit of the power pack is protected by a 10 mA fuse. The output voltage of the power pack is available at the terminals 209 and 210. These terminals can also be extended outside of the device to an external supply with an external power pack or an external 12 volt battery. This, for example, can be necessary when the apparatus is operated in an automobile. The low-voltage region is again protected by a 100 mA fuse. This fusing is coupled to two 20 volt Zener diodes of 2.5 watts each.

The Zener diodes have the following function. If the transformer were to receive a short from the primary winding to the secondary winding and the power consumption of the power pack in the primary region remains below 10 mA, a voltage of 220 volts would be applied at the terminals 209 and 210. Since this voltage is greater than 20 volts, the Zener diodes would immediately become conductive and would therefore allow the 100 mA fuse to separate. Each of the 20 volt Zener diodes is capable of this function.

The system therefore has the following devices available in the apparatus for protecting the patient against overvoltages;
1. A 10 mA fuse preceding the powerpack;
2. A dual-pole on/off switch $a_1$;
3. A galvanic separation of 220 volts and 12 volts on the basis of primary and secondary windings;
4. A 100 mA fuse before the entrance to the low-voltage section;
5. Two Zener diodes which work independently of one another for triggering the fusing in the low-voltage region; and
6. Operation of the sensor input portion in the micro-volt range.

With respect to the mattress, the PVC insulating film protects the entire mat and the grounded aluminum foil shields the entire capacitor.

Since there is a requirement that all unnecessary displays should be disconnected given emergency operation/ battery operation, primarily in order to save energy and to therefore extend the possible emergency operating time, the displays for the commercial voltage (107) and respiratory function (102) are only introduced into the circuit of the commercial power supply devices, i.e. given outage of the power pack, the current from these two displays can no longer flow to ground since a diode inhibits the circuit. The negative pole of the moving coil instrument 101 and of the alarm diode 103 and the battery indicator remain uneffected by this operation. The power pack having an output voltage of 12 volts DC simultaneously feeds the emergency battery which is connected to a terminal 211 and to the negative terminal 212. An additional resistor is provided, this resistor having the function of effecting the current limitation given long-term charging battery. The normal voltage of the battery amounts to about 10.8 volts, so that there is always an adequate potential gradient, for example, 1.2 volts each from 9 rechargeable cells. Due to the resistor designed for 100 ohms, the charging current is limited to 120 mA even given a completely uncharged battery. In normal operation, the charging current of the battery amounts to 20 mA. The assumed potential difference thereby amounts to 2 volts. The 100 ohm resistor is followed by a diode which prevents the battery from discharging via the secondary winding of the transformer or via the leakage currents of the Zener diodes in its unconnected condition.

The apparatus designed provides that a noise transmission alarm is integrated in the housing. In this case, the alarm signal can be taken at a point 207 of the circuit. It is meaningful to supply the noise transmission alarm and the apparatus via a central, stabilized power pack. The power pack would then feed the current at the points 209 and 210. The noise transmission alarm is intended to meet the following functions:
1. Transmission of the alarm (always); and
2. Transmission of the noise in, for example, a nursery (selection should be possible by defining the response threshold).

The integration of the transmitter into the housing prevents the danger that the transmitter and the receiver, having nearly all identical design, could be confused with one another. Under given conditions, it may also be meaningful for the noise alarm to be operated alone, in particular when the patient has grown out of the at-risk age and is no longer in need or respiratory monitoring.

Although I have described my invention by reference to particular illustrative embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. An apparatus for monitoring at least one life function of a life form, comprising:
a voltage source;
support means for supporting the life form including a resilient mat, a capacitance means mounted insulated in the mat connected to said voltage source and responsive to movements of the life form to produce life function signals representing such movements; and
a monitoring unit coupled to said capacitance means and including a high-impedance first amplifier stage for receiving the life form signals, said high-impedance first amplifier stage having an input impedance on the order of 500K ohms or greater;

a second amplifier stage connected to said first amplifier stage for amplifying the life form signals by a first factor;

first filter means connected to said second amplifier stage for filtering out commercial supply hum and high frequencies at least above about 50 hz;

second filter means connected to said first filter means for filtering out any DC voltage components;

a third amplifier stage connected to said second filter means for amplifying the life form signals by a second factor;

third filter means connected to said third amplifier stage for filtering out commercial hum and high frequencies at least above about 50 hz; and an image recognition and display means connected to said third filter means and operable to compare the life form signals to stored predetermined life form signals and produce an alarm when the current life form signals transgress a predetermined tolerance range.

2. The apparatus of claim 1, wherein: said mat and said capacitance means comprise first and second insulation layers, a first electrode sandwiched between said first and second layers and connected to ground, second and third electrodes carried on said first and second layers for connection to said first amplifier stage and forming respective capacitors with said first electrode, third and fourth insulation layers respectively carried on said second and third electrodes, and a fourth electrode spaced from said second and third electrodes by said third and fourth insulation layers and converted to said first electrode and forming respective capacitors with said second and third electrodes.

3. The apparatus of claim 2, wherein: each of said electrodes comprises an aluminum layer.

4. The apparatus of claim 2, and further comprising: punctiform adhesive means securing said electrodes and insulation layers together.

5. The apparatus of claim 2, and further comprising: a textile cover on said mat.

6. The apparatus of claim 2, wherein said first amplifier stage comprises:

a pair of amplifiers each connected to said second and third electrodes for receiving offset life form signals.

7. Apparatus for monitoring at least one life function of a life form, comprising:

a voltage source;

support means for supporting the life form including a resilient mat, a capacitance means mounted insulated in the mat connected to said voltage source and responsive to movements of the life form to produce life function signals representing such movements; and a monitoring unit coupled to said capacitance means and including a high-impedance first amplifier stage for receiving the life form signals, said high-impedance first amplifier stage having an input impedance of about 500K ohms;

a second amplifier stage connected to said first amplifier stage for amplifying the life form signals by a first factor;

first filter means connected to said second amplifier stage for filtering out commercial supply hum and high frequencies at least above about 50 hz;

second filter means connected to first filter means for filtering out any DC voltage components;

a third amplifier stage connected to said second filter means for amplifying the life form signals by a second factor;

third filter means connected to said third amplifier stage for filtering out commercial hum and other high frequencies at least above about 50 hz; and a fourth amplifier stage connected to said third filter means for amplifying the life function signals by a third factor;

a comparator connected to said fourth amplifier stage for comparing the life function signals to a predetermined reference and operable to produce an output signal when the life form signal transgress the reference;

a relay operable to produce an alarm signal; and a relay drive connected between said comparator and said relay and including timing means causing integration of said output signals and operation of said relay when the integrated signal transgresses a reference level.

8. The apparatus of claim 7, wherein:

said comparator and said relay driver each include variable reference setting means.

9. The apparatus of claim 7, wherein:

said relay is a latching relay.

10. The apparatus of claim 7, and further comprising: fourth filter means connecting said third filter means to said fourth amplifier stage and operable to remove a DC voltages from the life function signals.

11. The apparatus of claim 7, wherein:

said first and third filter means each comprise an active filter.

* * * * *